(12) United States Patent
Berghaus et al.

(10) Patent No.: US 11,988,588 B2
(45) Date of Patent: May 21, 2024

(54) MULTI-FIBRE OPTICAL PROBE

(71) Applicant: COLVISTEC AG, Berlin (DE)

(72) Inventors: Andreas Berghaus, Berlin (DE); Oliver Kohler, Berlin (DE)

(73) Assignee: COLVISTEC AG, Berlin (DE)

( * ) Notice: Subject to any disclaimer, the term of this patent is extended or adjusted under 35 U.S.C. 154(b) by 339 days.

(21) Appl. No.: 17/614,883

(22) PCT Filed: May 29, 2020

(86) PCT No.: PCT/EP2020/065071
§ 371 (c)(1),
(2) Date: Nov. 29, 2021

(87) PCT Pub. No.: WO2020/240015
PCT Pub. Date: Dec. 3, 2020

(65) Prior Publication Data
US 2022/0236162 A1    Jul. 28, 2022

(30) Foreign Application Priority Data

May 29, 2019 (GB) ..................... 1907572

(51) Int. Cl.
*G01N 15/0205* (2024.01)
*A61B 1/07* (2006.01)

(52) U.S. Cl.
CPC ............ *G01N 15/0205* (2013.01); *A61B 1/07* (2013.01); *G01N 15/0211* (2013.01)

(58) Field of Classification Search
CPC ........... G01N 15/0205; G01N 15/0211; G01N 2021/8411; G01N 21/8507;
(Continued)

(56) References Cited

U.S. PATENT DOCUMENTS

| | | | |
|---|---|---|---|
| 4,684,488 A | 8/1987 | Rudolph | |
| 5,606,170 A * | 2/1997 | Saaski | G01N 21/7703 250/227.14 |

(Continued)

FOREIGN PATENT DOCUMENTS

| | | |
|---|---|---|
| EP | 1 319 939 | 6/2003 |
| EP | 2107401 | 10/2009 |

(Continued)

OTHER PUBLICATIONS

Aliyu et al., "Development of a dual optical fiber probe for the hydrodynamic investigation of a horizontal annular drive gas/liquid ejector," *Flow Measurement and Instrumentation*, 56:45-55 (Aug. 2017).

(Continued)

*Primary Examiner* — Jonathan M Hansen
(74) *Attorney, Agent, or Firm* — Klarquist Sparkman, LLP

(57) ABSTRACT

A multi-fibre optical probe for spectroscopically analysing high concentration mediums (i.e. about 40 wt % or higher solid particulates), an extruder comprising a multi-fibre optical probe, use of said multi-fibre optical probe are provided. Methods of generating a predictive model, determining the value of a parameter of a solid particulate dispersion and manufacturing a solid particulate dispersion are also provided.

35 Claims, 5 Drawing Sheets

(58) Field of Classification Search
CPC ........... G01N 2021/8528; G01N 21/01; G01N 2021/0112; A61B 1/07
See application file for complete search history.

(56) References Cited

U.S. PATENT DOCUMENTS

| | | | | |
|---|---|---|---|---|
| 5,740,291 | A | * | 4/1998 | De Lasa ................ G01N 21/49 250/227.24 |
| 6,411,373 | B1 | * | 6/2002 | Garside ................ G01N 21/474 385/115 |
| 2009/0252451 | A1 | | 10/2009 | Lagakos et al. |
| 2014/0219613 | A1 | | 8/2014 | Nielson et al. |
| 2016/0022119 | A1 | * | 1/2016 | Shahmoon ......... A61B 1/00167 600/182 |
| 2021/0018744 | A1 | * | 1/2021 | Rigneault .......... A61B 1/00167 |
| 2021/0022827 | A1 | * | 1/2021 | Piao ....................... A61B 34/37 |

FOREIGN PATENT DOCUMENTS

| | | |
|---|---|---|
| EP | 2266453 | 12/2010 |
| JP | 2005 192612 | 7/2005 |
| WO | WO 2015/118525 | 8/2015 |

OTHER PUBLICATIONS

Magnusson et al., "Dual fibre optical prove measurements of solids volume fraction in a circulating fluidized bed," *Powder Technology*, 151(1-3):19-26 (Mar. 2005).

International Search Report and Written Opinion for related International Application No. PCT/EP2020/065071, 17 pages, dated Nov. 26, 2020.

Hass et al. "Industrial applications of Photon Density Wave spectroscopy for in-line particle sizing [Invited]," *Applied Optics*, 52(7):1423-1431 (Feb. 25, 2013).

Search Report for related European Application No. GB 1907572.0, 7 pages, dated Nov. 12, 2019.

* cited by examiner

MULTI-FIBRE OPTICAL PROBE

CROSS REFERENCE TO RELATED APPLICATIONS

This is the U.S. National Stage of International Application No. PCT/EP2020/065071, filed May 29, 2020, which was published in English under PCT Article 21(2), which in turn claims the benefit of GB Application No. 1907572.0, filed May 29, 2019, which is incorporated herein in its entirety.

FIELD OF THE DISCLOSURE

The present invention relates to a multi-fibre optical probe comprising optical fibres, an extruder comprising the multi-fibre optical probe and use of the multi-fibre optical probe.

BACKGROUND

Optical probes are devices that can be used to measure the properties of a medium using light. Such probes may be configured to measure one or more of the light transmittance, absorption and scattering properties of the medium.

Highly concentrated mediums, such as solid particulates dispersed in liquid suspensions or solutions, are difficult to analyse by absorbance or transmission spectroscopy. This is because optical probes often measure changes in absorption or transmission of light over a relatively large light path by positioning the illumination source and detector far apart. The high optical density of highly concentrated mediums prevents any meaningful measurement by absorbance or transmission spectroscopy.

A standard light path length of, for example, an in-line probe for an extruder, is in the order of a few millimetres or greater, for example, 1 mm to 300 mm. Also known are attenuated total reflectance (ATR) probes. These probes are essentially surface probes that are only useful for looking at dissolved molecules. A sample is put in direct contact with an ATR crystal and a light path is formed by total reflection through the crystal. The typical light path length through the ATR crystal is, for example, 0.5 to 2 microns. ATR probes are not suitable for looking at particulate dispersions where the particle size is larger than the wavelength of light.

At high concentrations (i.e. about 40% or greater solid particulates) these light paths have the problems of saturation and total attenuation of the incident light by absorption or scattering. It is therefore not possible to use surface, transmittance, reflectance or absorbance spectroscopy to conduct in-line measurements of highly concentrated mediums. On-line optical measurements are typically made by extraction of one or more samples from the ongoing process and diluted for at-line or off-line analysis.

One high concentration medium that suffers from the aforementioned optical analysis difficulties is masterbatch—a mixture of a solid carrier (40 to 50 wt %), typically a polymer or a wax, and pigments or additives that are optimally dispersed in the solid carrier at high concentrations (50 to 60 wt %). Pigments are added to and dispersed in the heat melted carrier which is then cooled to form the final solid masterbatch product. This is often performed as a hot melt extrusion process. Masterbatch may then be used economically in subsequent manufacturing processes as an additive to colour plastics and other products.

The polymer or wax of the masterbatch is typically chosen to match the intended host material of the final product into which it will be incorporated. In particular, because it is difficult to accurately spectroscopically analyse high concentration mediums, it is also difficult to determine parameters that correlate to spectroscopic data, such as particle size distribution in masterbatch, or partial dilutions thereof.

It is challenging to spectroscopically analyse the properties of masterbatch in its most concentrated state. Because the spectral properties of masterbatch are related to particle loading amount, particle size distribution, particle distribution (homogeneity), concentration, crystallinity, colour strength and aggregation state, which can vary from batch to batch, it is often insufficient to rely on weight alone when formulating a coloured polymer mixture.

Determination of a masterbatch parameter, such as particle size distribution, provides an excellent predictor of final product performance. This is because particle size distribution is directly related to appearance, quality, functionality and processability of masterbatch. Accurate in-line monitoring of particle size distribution therefore represents an important goal for providing good quality coloured products.

For pigments, the particle size distribution affects the final colour and colour strength. If the pigment particles are too large, then the internal part of the particle is essentially not utilised because light only interacts with the surface and does not penetrate through the particle. This means that the amount of pigment needed to reach a particular colour may change if the particle size distribution is varied. In reality, the pigment is repeatedly milled (in an off-line process) to get the particle size down.

The preferred parameters, such as particle size distribution, vary according to the desired result. The present invention allows the operator to make informed decisions based on live (e.g. in-line) or upstream (e.g. during milling) data to optimise the process.

Because of the aforementioned problems, in-line monitoring of masterbatch production by extrusion is not currently known.

The spectroscopic in-line monitoring of the colour of a finally diluted plastic product at the outlet of an extruder is well known. For example, U.S. Pat. No. 4,684,488 describes a method and apparatus for controlled supply of colour concentrates into an extruder to obtain a plastic product of the desired colouration.

Magnusson et al. *Powder Technology*, 2005, 151, 19-26 describes a dual fibre optical probe for the measurement of solid volume fraction in a circulating fluidized bed. A reflectance measurement is made through a glass measurement window using an angled dual-fibre probe to continuously measure the solid fraction of a solid in a gas particle suspension. As explained above, a standard reflectance measurement is not suitable for measuring the properties of a high concentration medium such as masterbatch.

WO 2015/118525 A1 describes the in-line colour strength measurement of extrudate by optical spectroscopy, comparing it to a reference material and controlling the feeding device of a dispensing system by using the signal obtained from the comparison and the processing of spectral properties. This document does not describe or suggest the in-line optical measurement of a high concentration medium and only the properties of the final product are measured.

According to Reich et al. *Applied Optics* 2013 52(7) 1423-31, Photonic Density Wave (PDW) spectroscopy has been used for measuring and quantifying light absorption and scattering in dense mediums. This technique uses a laser light source and an illumination fibre to analyse high concentration heterogeneous phases in batch processes. It is possible to measure the particle size of a suspended solid using this technique.

However, PDW spectroscopy has never been demonstrated in-line with an extruder or other flow-based system. Furthermore, PDW spectroscopy requires complex mathematical processing of the data, information on the refractive index of each component in the medium and high intensity modulated laser light.

Aliyu et. al. *Flow Measurement and Instrumentation* 2017, 56, 45-55 describes a dual fibre probe where two fibres having a tip-to-tip separation along the axis of the fibre length of 600 microns for quantifying bubble characteristics in gas-liquid systems. The probe was used in reflectance mode to measure void fraction, bubble diameter and velocity in flow. As explained above, a standard reflectance measurement is not suitable for measuring the properties of a high concentration medium. Furthermore, a dual fibre probe does not provide enough intensity for a photodetector to make reliable measurements of high concentration mediums.

The present disclosure has been devised in the light of the above considerations.

SUMMARY OF THE DISCLOSURE

Optical Fibre for a Multi-Fibre Optical Probe

In a first aspect there is provided an optical fibre for a multi-fibre optical probe for the in-line spectroscopic monitoring of high concentration mediums comprising a transparent core circumferentially coated by a cladding that is 25 microns or less in thickness. For example, the coating may be 20, 15, 10, 9, 8, 7, 6, 5, 4, 3, 2 or 1 micron(s) or less.

The cladding thickness in currently known optical fibres is typically greater than about 25 microns and thereby prevents the ends of the optical fibres being arranged in parallel with a distance of less than about 50 microns between them. Moreover, there does not presently exist an optical fibre having the required inner diameter to provide sufficient light intensity with a low thickness cladding that allows close arrangement of the optical fibre ends.

In some cases, the optical fibre is a glass optical fibre. Preferably, the glass is one of fluorozirconate, fluoroaluminate, chalcogenide sapphire or silica glass (quartz). More preferably the glass is silica glass. The silica may be fused silica. The term glass optical fibre does not include hard-clad silica fibres (HCSFs) or plastic optical fibres (POFs).

In some instances, the optical fibre has a core diameter of 800 microns or less, such as 600, 400, 200, 100, 80, 60, 40 or 20 microns or less. The core diameter may be 50, 100, 200, 300, 400 or 500 microns or more.

In some cases, the optical fibre consists of only two layers; the transparent core and the cladding. This is fewer than the typical three-layers found in a single mode optical fibre having an intermediate doped quartz layer. This extra intermediate layer of the prior art has a very different refractive index to the core material to prevent light leaking from the fibre. However, the present two-layer optical fibre achieves excellent light intensity along the cable length without an intermediate layer or any external plastic cladding.

In some cases, the optical fibre cladding comprises a metal and/or metal oxide. Preferably, the metal is one or more of gold, rhodium, palladium, nickel, iron, cobalt, ruthenium, iridium, osmium, zinc, copper, silver, chromium, molybdenum, tungsten, vanadium, niobium, tantalum, titanium, zirconium or hafnium. The cladding may also be made of oxides of these metals, or metal compounds or alloys.

Preferably, the cladding comprises, or more preferably consists of, chromium. The cladding may comprise a polyimide.

Preferably, the optical fibre is cladded along its entire length at the specified thickness. However, the cladding thickness is most important at an end of the fibre to be used at the head of a probe. Therefore, the cladding thickness at other points along the length of the optical fibre is not particularly limited so long as it does not prevent an end of the optical fibre from being arranged in close proximity to an end of a similar optical fibre to form a small light path that is, for example, 50 microns or less in length. The end faces of the optical fibre are partially or completely free from cladding to allow light input and light output.

Multi-Fibre Optical Probe

In a second aspect of the invention, there is provided a multi-fibre optical probe for in-line spectroscopic monitoring of high concentration mediums comprising; at least one light detection fibre wherein each light detection fibre is for receiving light at a light receiving end, and at least two illumination fibres for emitting light from a light emitting end; wherein the number of illumination fibres is equal to or greater than the number of light detection fibres, and the light emitting ends of each of the illumination fibres are each independently positioned 50 microns or less from the light receiving end of at least one light detection fibre.

The multi-fibre optical probe provided has at least two illumination fibres. Having a plurality of illumination fibres increases the intensity of received light that is scattered by high concentration mediums, which is otherwise very low.

Furthermore, the optical fibres are positioned to form micrometre scale light paths between the illumination fibres and the light detection fibre(s). The light paths are the small distances between each light emitting end of the illumination fibres and the light receiving end of one or more corresponding light detection fibres. These light paths may be occupied by a correspondingly sized amount of high concentration medium.

Using small light paths prevents significant attenuation of scattered light and facilitates the spectroscopic analysis of concentrated mediums. Although the present multi-fibre optical probe has the advantage of being able to spectroscopically analyse high concentration mediums (i.e. having greater than 40 wt % solid particulates) it may also be used to spectroscopically analyse low concentration mediums (i.e. having less than 40 wt % solid particulates).

Together, the plurality of illumination fibres, one or more light detection fibres and micrometre scale light paths ensure that the intensity of the scattered light is above a detectable threshold and so may be used to reliably gather spectral data.

The spectral data may then be used to determine parameters that show correlation with one or more optical characteristics of the mediums. For example, CIELAB colour parameters show a correlation with particle size distribution. A predetermined model can be used to provide good quantitative accuracy of parameter determination.

Illumination of a concentrated medium typically forms a small sphere of diffused scattered light that is detected at the light receiving end of the detection fibres. Changes in the spectrum of the light scattered by high concentration mediums may be measured for each light path.

Other suitable optical probe setups are also contemplated. For example, the glass optical fibres may be substituted by suitable plastic optical fibres or co-axial optical cables so long as an appropriate light path is provided to achieve the desired technical effects. It is also contemplated that the light path may be formed by a suitable arrangement of prisms, for example.

In some cases, the light receiving fibres and illumination fibres are each independently according to the first aspect. Optical fibres provided for other uses are not typically suitable for a multi-fibre optical probe of the present type. For instance, adjacent optical fibres in telecommunications are designed to avoid 'cross talk' with each another to preserve the data being carried by each fibre. This would not suit the present multi-fibre optical probe which relies on light from the end of an illumination fibre reaching the end of a light detecting fibre. Telecommunication optical fibres are also typically 5 to 10 μm diameter single-mode fibres with a 125 μm cladding that are designed to transmit coherent light in a very specific narrow wavelength range. Optical fibres for endoscopes are typically provided in arrangements to detect reflected light through air at a distance from the subject. None of these known optical fibres are designed with spectroscopic analysis in mind. By contrast, the present optical probe may be immersed in high concentration mediums where the ends of the optical fibres are then in direct contact with the high concentration mediums (i.e. without air or gas between them) and are in optical contact with some or all of the other optical fibres.

In some cases, the multi-fibre optical probe is set to transmission mode. That is to say, the probe is configured for transmission spectroscopy. The small light path makes a transmission measurement of a high concentration medium possible when the ends of the probe are positioned in the high concentration medium. Due to their mathematical relationship, where a transmission spectrum is acquired it follows that an absorbance spectrum can be derived therefrom, and vice versa.

In some cases, the light receiving fibres and illumination fibres are each independently multi-mode fibres. That is to say, they are able to transmit white light of a broad spectrum from many incidence angles.

In some cases, the or each light detecting fibre and the illumination fibres are each free of additives comprising germanium and/or chlorine. The light detecting fibres and illumination fibres may each be free of any additives. That is to say, the optical fibres are not doped. This ensures that the optical fibres operate on the maximum spectrum of wavelengths possible; something that is not possible in fibres doped to auto-fluoresce, for example. Providing optical fibres free of additives also ensures that no other compounds are present that could interact or react with the high concentration mediums when in use.

In some instances, the number of illumination fibres is greater than the number of light detection fibres. This configuration is particularly preferred to provide the light intensity for improved accuracy.

In some cases, the light emitting ends of each of the at least two illumination fibres are each independently positioned between 5 to 45 microns, such as between 10 to 40 microns, 15 to 35 microns, or 20 to 30 microns, from the light receiving end of the at least one light detection fibre.

In some instances, the light receiving ends of each of the at least two light detection fibres are each positioned equidistantly from the light emitting end of the at least one illuminating fibre.

In some cases, each light detection fibre is connected to a photodetector and each illumination fibre is connected to a light source.

In some instances, each light detection fibre is connected to the same photodetector and each illumination fibre is connected to the same light source.

In some cases, one or more of the light detection fibres are connected to a dedicated photodetector. For example, all of the light detection fibres may be connected to their own dedicated photodetector. This includes, for example, a hyperspectral imaging whereby each light detection fibre is connected to one or more dedicated pixels of a staring array.

In some instances, one or more of the illumination fibres are connected to a dedicated light source. For example, all of the illumination fibres may be connected to their own dedicated light source.

In some cases, the or each photodetector is configured to detect light at wavelengths of from UV to mid-IR, such as 190 to 5000 nm, 190 to 2500 nm or 190 to 900 nm. The or each photodetector may be independently configured to detect light at the same or different wavelengths. For example, all of the photodetectors may be configured to detect light at the same wavelengths.

In some cases, the or each light source is configured to emit light at wavelengths of from UV to mid-IR, such as 190 to 5000 nm, 190 to 2500 nm or 190 to 900 nm. The or each light source may be independently configured to detect light at the same or different wavelengths. For example, all of the light sources may be configured to emit light at the same wavelengths.

In some instances, the total number of optical fibres in the multi-fibre optical probe is 50 or more, such as 100 or more, 250 or more, 500 or more, 1,000 or more or 2,000 or more.

In some cases, the ratio of light receiving fibres to illumination fibres is 1 to 6 respectively. For example, the multi-fibre optical probe may comprise 1 light detection fibre and 6 illumination fibres.

In some instances, the ratio of light detection fibres to illumination fibres is 7 to 12 respectively. For example, the multi-fibre optical probe may comprise 7 light detection fibres and 12 light detection fibres.

In some cases, the light illumination fibres are arranged substantially around the one or each light detection fibre. An advantage of this arrangement is that the light paths are concentrated towards a central light detection fibre to provide a higher intensity signal.

In some instances, the multi-fibre optical probe does not comprise a window between and/or in front of the light emitting end of the light emitting fibre and any of the light receiving ends of the light detection fibres. Windows that are used in conventional spectroscopy are not generally compatible with the multi-fibre probe of the second aspect because they are too bulky and prevent the ends of the optical fibres from being arranged in close enough proximity, to each other and to a high concentration medium. Moreover, the multi-fibre optical probe may not comprise any structure covering and/or in front of the ends of the optical fibres at the tip of the multi-fibre optical probe, particularly if the structure can interact with or react to light from the optical fibres. The ends of the optical fibres at the tip of the multi-fibre optical probe are free such that they can be brought into direct contact with a high-concentration medium by immersion. This way, the previously mentioned small sphere of diffused light is formed in close proximity to or at the tip of the multi-fibre optical probe such that the light may be adequately detected via the one or more light detection fibres.

In some cases, each optical fibre independently has a core diameter of 800 microns or less, such as 600, 400, 200 or 100 microns or less. The core diameter may be between 8 to 400 microns or 50 to 200 microns. The core diameter may be 50, 100, 200, 300, 400 or 500 microns or more. The fibres work particularly well in the probe when the core diameter is 50 microns or more, especially 100 microns or more. The core diameter refers to the transparent inner core of an optical fibre. This is sometimes referred to as the inner diameter. Each optical fibre may each independently have the same or a different core diameter. For instance, the illumination fibres may each have the same or different core diameters. Where there are multiple detection fibres, the detection fibres may each have the same or different core diameters.

In some instances, each optical fibre independently comprises cladding having a thickness of 25 microns or less such as between 1 to 20 microns or 5 to 15 microns. Preferably the cladding thickness is 10 microns.

In some cases, the optical fibres are provided so that the light emitting ends are substantially parallel to each another in the same direction. Sometimes, part or all of the lengths of the optical fibres are also substantially parallel to each other. The optical fibres are optionally provided in a secured fibre bundle.

It is theorised that the parallel arrangement of the fibres allows for a more accurate measurement in the change in absorbance of scattered light because it is measured across micrometre sized 'open' light paths. This is in comparison to, for example, an equivalent transmission measurement across a transverse 'closed' light path where the light source and detector are positioned either side of the medium to form a physically restrictive 'closed' light path that larger particles may be excluded from entering.

Extruder Comprising a Multi-Fibre Optical Probe

In a third aspect there is provided an extruder comprising a multi-fibre optical probe, optionally according to the second aspect, wherein the optical probe is positioned at one or more of the points of solid particulate input, upstream of the point of extrusion and the point of extrusion.

In some cases, the multi-fibre optical probe is positioned such that when in use the ends of the fibres are immersed in the material being extruded such that the light paths between the ends of the illumination fibres and the ends of the light detection fibre(s) pass through the material.

Use of a Multi-Fibre Optical Probe

In a fourth aspect there is provided use of a multi-fibre optical probe, optionally according to the second aspect, to obtain a spectrum of the light scattered by a high concentration medium. That is to say, a spectrum of the light transmitted through the high concentration medium in the diffuse sphere of light.

In some instances, the high concentration medium is a medium having an optical density at which a reliable spectrum cannot be obtained by standard absorbance or transmission spectroscopic methods.

In some cases, the ends of the fibres of the multi-fibre optical probe are positioned in a high concentration medium such that the light paths between the ends of the illumination fibres and the ends of the light detection fibre(s) pass through the high concentration medium.

In some instances, the spectrum is a transmission spectrum.

In some cases, the high concentration medium is a medium having an optical density of 4 (0.01% transmission) or more. Preferably, the optical density is 5 (0.001% transmission), 6 (0.0001% transmission) or 7 (0.00001% transmission) or more. Most preferably, the medium has an optical density of 6 (0.001% transmission) or more. The values given are as measured at a wavelength of 600 nm ($OD_{600}$).

In some instances, the spectrum is used in any one or more of the methods disclosed herein.

Method of Generating a Predictive Model

In a fifth aspect there is provided a method of generating a predictive model for determining the value of a parameter of a solid particulate dispersion comprising the steps of; (i) spectroscopically analysing a plurality of reference samples of solid particulate dispersions spanning a range of values of the parameter using a multi-fibre optical probe, (ii) measuring a spectrum of each reference sample, and (iii) processing the spectra gathered in step (ii) to generate a predictive model that correlates the parameter to one or more spectroscopic properties.

In some instances, the number of reference samples is 5 or more.

In some cases, the spectra are pre-processed before step (iii) to normalise and/or smooth the spectra.

In some instances, the spectra of the reference samples are processed to derive a feature that correlates with the parameter across at least a portion of said range of the parameter.

In some cases, said feature comprises: at least a first principle component derived from principle components analysis (PCA) of all or part of the spectra or a parameter derived from the spectra (such as a CIELAB colour space parameter), optionally wherein the variance of said first principle component by the parameter is substantially linear across the range the parameter of said plurality of dispersions; or one or more of a lightness value L*, an a* colour value or a b* colour value of CIELAB colour space derived from the spectra.

In some instances, the ends of the fibres of the multi-fibre optical probe are positioned in the solid particulate dispersion such that the light paths between the ends of the illumination fibres and the ends of the light detection fibre(s) pass through the solid particulate dispersion.

In some instances, the spectra are transmission spectra.

In some cases, the multi-fibre optical probe is according to the second aspect.

In some cases, the solid particulate dispersion has an optical density of 4 (0.01% transmission) or more. Preferably, the optical density is 5 (0.001% transmission), 6 (0.0001% transmission) or 7 (0.00001% transmission) or more. Most preferably, the dispersion has an optical density of 6 (0.001% transmission) or more. The values given are as measured at a wavelength of 600 nm ($OD_{600}$).

Method of Determining the Value of a Parameter of a Solid Particulate Dispersion In a sixth aspect there is provided a method of determining the value of a parameter of a solid particulate dispersion comprising the steps of; (i) subjecting the dispersion to spectroscopy using a multi-fibre optical probe, (ii) measuring the spectrum of the dispersion, and (iii) determining the value of the parameter by comparing the observed spectrum to a predictive model.

In some cases, the predictive model is generated according to the fifth aspect.

In some cases, comparing the observed spectrum to the predictive model comprises processing the observed spectrum in the same way as the spectra of said plurality of reference samples.

In some instances, the ends of the fibres of the multi-fibre optical probe are positioned in the solid particulate dispersion such that the light paths between the ends of the illumination fibres and the ends of the light detection fibre(s) pass through the solid particulate dispersion.

In some instances, the spectra are transmission spectra.

In some cases, the multi-fibre optical probe is according to the second aspect.

In some cases, the solid particulate dispersion has an optical density of 4 (0.01% transmission) or more. Preferably, the optical density is 5 (0.001% transmission), 6 (0.0001% transmission) or 7 (0.00001% transmission) or more. Most preferably, the dispersion has an optical density of 6 (0.001% transmission) or more. The values given are as measured at a wavelength of 600 nm ($OD_{600}$).

Method of Manufacturing a Solid Particulate Dispersion

In a seventh aspect there is provided a method of manufacturing a solid particulate dispersion comprising the steps of; (i) forming a solid particulate into an dispersion, (ii) determining the value of the parameter of the dispersion one or more times by the method of the sixth aspect, and (iii) where the dispersion has a parameter value within an acceptable range, processing the dispersion into a finished product.

In some cases, the forming of the solid particulate into a dispersion is performed by extrusion; and/or the testing of the parameter value one or more times is performed in-line.

In some instances the forming is performed by extrusion and the testing is performed at one or more of the point of solid particulate input, upstream of the point of extrusion and at the point of extrusion.

The following features may apply independently to any of the aspects, instances or cases of the aforementioned uses or methods. The extrusions may be hot melt extrusions. The solid particulate may be a pigment. The solid carrier may be a polymer or wax. The finished product may be masterbatch. The parameter may be particle loading amount, particle size distribution, particle distribution (homogeneity), concentration, crystallinity, colour strength and aggregation state. The multi-fibre optical probe may be according to the second aspect. Any feature of the multi-fibre optical probe disclosed is any aspect of the invention herein is also applicable in any other aspect of the invention.

SUMMARY OF THE FIGURES

So that the invention may be understood, and so that further aspects and features thereof may be appreciated, embodiments illustrating the principles of the invention will now be discussed in further detail with reference to the accompanying figures, in which.

DETAILED DESCRIPTION

Figure 1B:
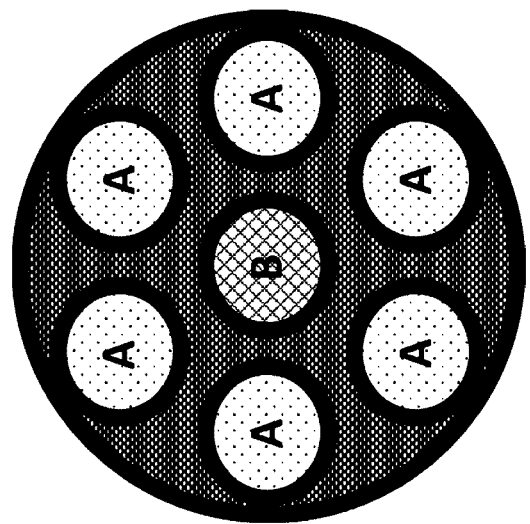
FIG. 1b shows a cross section of a multi-fibre optical probe similar to that of FIG. 1a, except that the fibres are provided in a steel tube sleeve and the interstitial space is filled with a binder.
Figure 1A:
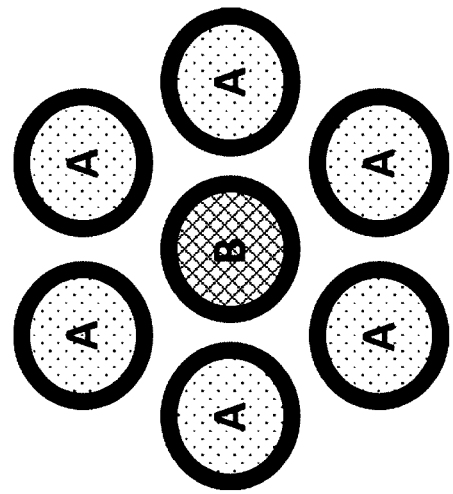
FIG. 1a shows a cross section of a multi-fibre optical probe having 6 illumination fibres (A) substantially arranged around a central light detection fibre (B).
Figure 2:
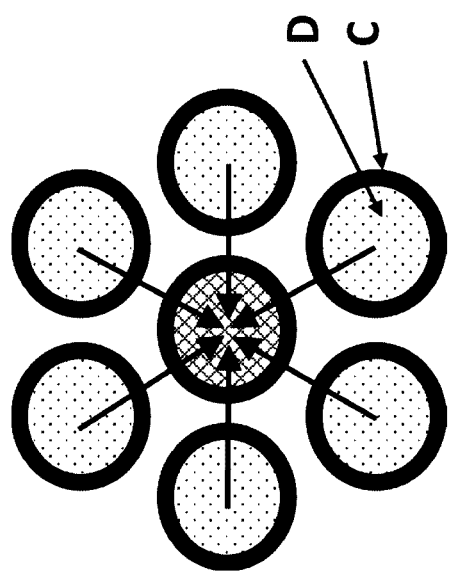
FIG. 2 shows a cross section of a multi-fibre optical probe as in FIG. 1 with arrows denoting the light paths from each illuminating fibre to the central light detection fibre. Furthermore, the fibre cladding (C) and fibre core (D) are also labelled.
Figure 3B:
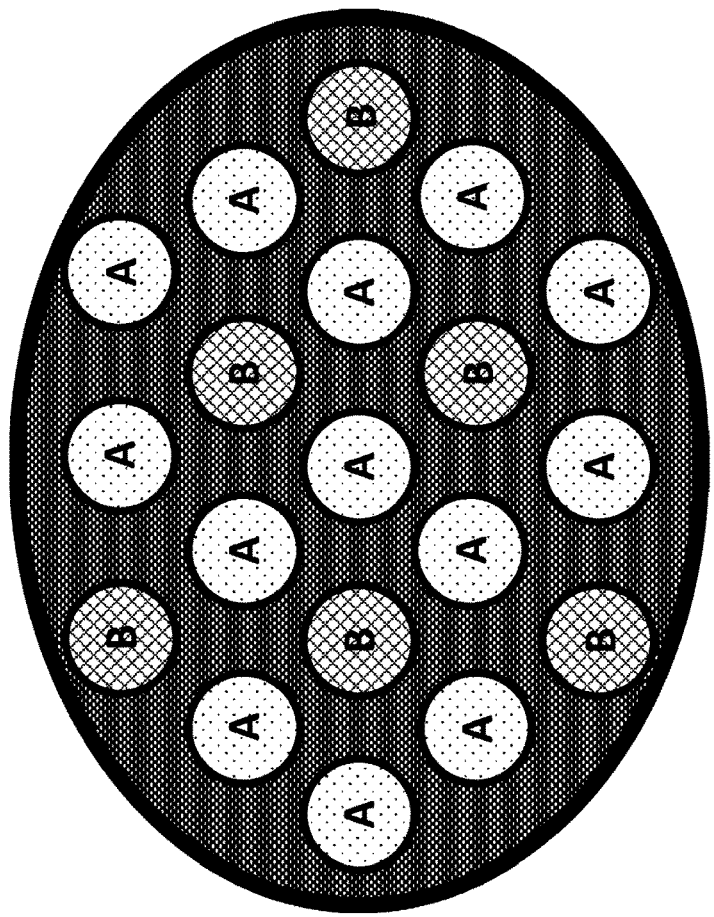
FIG. 3b shows a cross section of a multi-fibre optical probe similar to that of FIG. 3a, except that the fibres are provided in a steel tube sleeve and the interstitial space is filled with a binder.
Figure 3A:
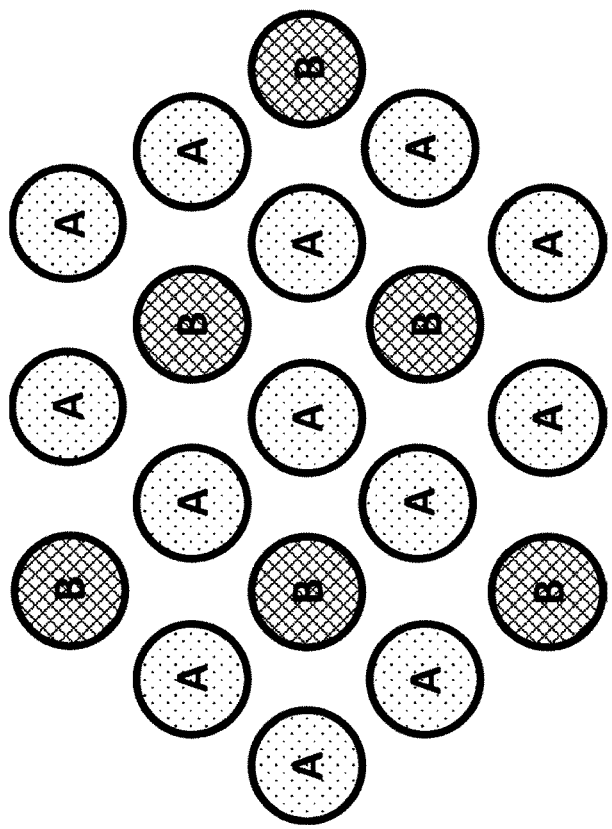
FIG. 3a shows a cross section of a multi-fibre optical probe having 12 illumination fibres (A) substantially arranged around 7 light detection fibres (B).
Figure 4:
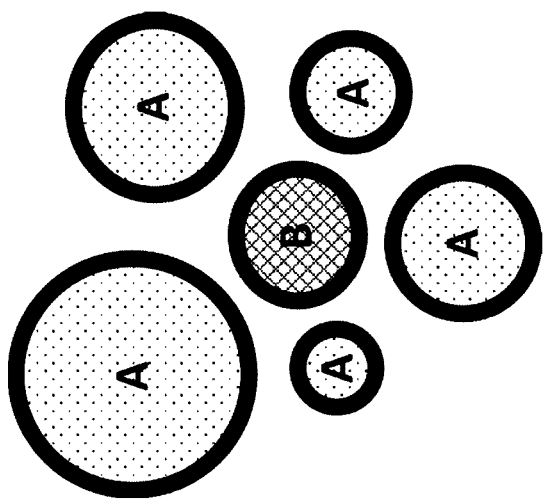
FIG. 4 shows a cross section of a multi-fibre optical probe having 5 illumination fibres (A), each having a different diameter, substantially arranged around 1 light detection fibre (B).

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the words "have", "comprise", and "include", and variations such as "having", "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means, for example, +/−10%.

The words "preferred" and "preferably" are used herein refer to embodiments of the invention that may provide certain benefits under some circumstances. It is to be appreciated, however, that other embodiments may also be preferred under the same or different circumstances. The recitation of one or more preferred embodiments therefore does not mean or imply that other embodiments are not useful, and is not intended to exclude other embodiments from the scope of the disclosure, or from the scope of the claims.

Examples

Method 1—Colour Parameter Measurement of Concentrated Red Paint Samples

A multi-fibre optical probe having 6 illumination fibres and 1 detection fibre was used to measure 3 samples of concentrated red paint. The optical fibres had a fused silica core and polyimide cladding. The concentration of the red paint samples was 1%, 5% and 25% w/w. The light path distance was 125 microns. The 3 paint samples were indistinguishable in colour by eye.

Analysis was conducted by immersing the tip of the multi-fibre optical probe into each of the 3 concentrated paint samples. The probe was connected to a spectrometer that was able to measure differences in the CIELAB colour parameters of each of the 3 paint samples. In each case, the concentrated paint was measured 3 times, and 3 or more measurements were taken per replicate.

Figure 5:
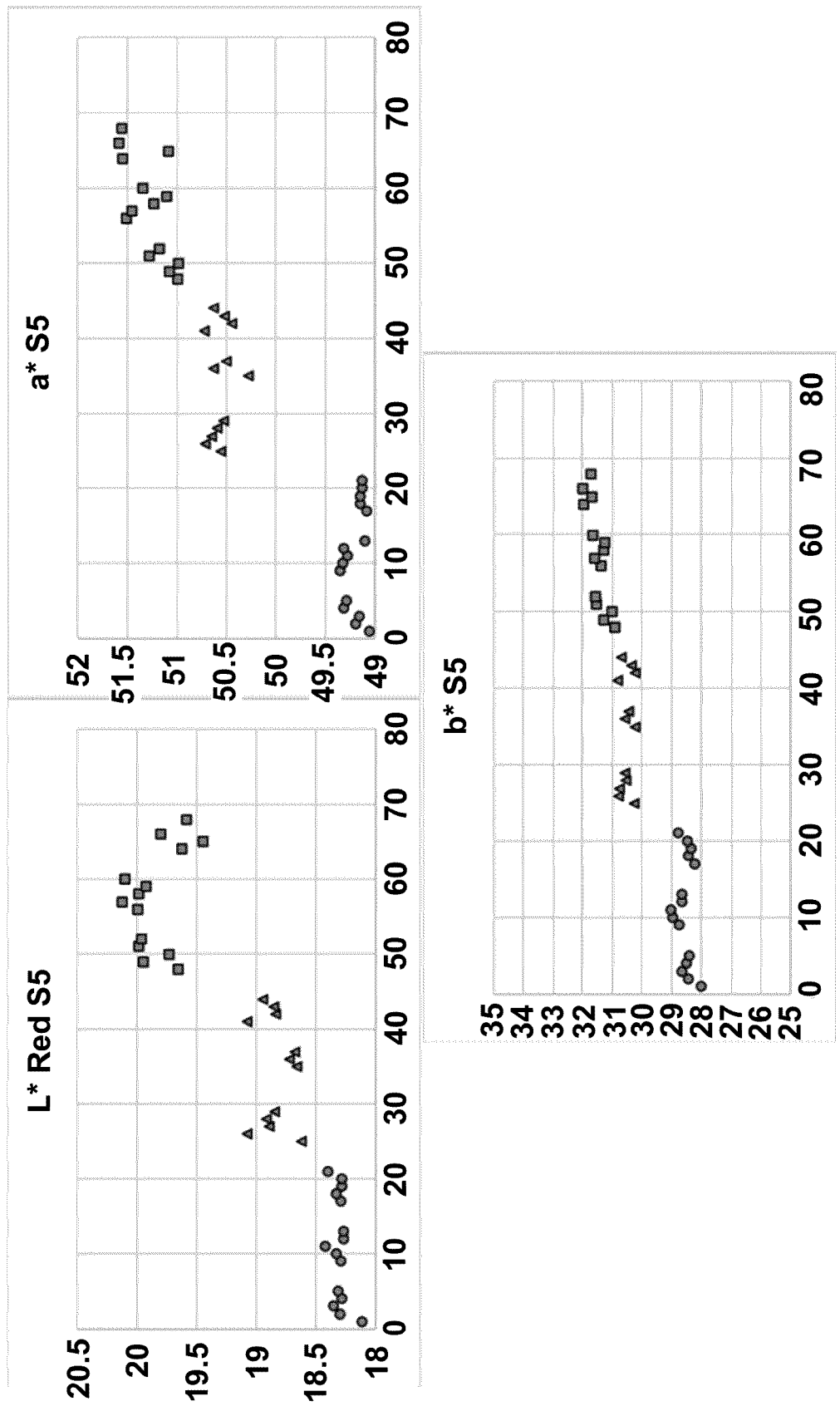
FIG. 5 shows the L*, a* and b* values obtained using a multi-fibre optical probe having 6 illumination fibres and 1 detection fibre to spectroscopically analyse 3 different concentrated red paint samples that were indistinguishable in colour by eye.

The CIELAB colour parameters measured are shown in FIG. 5. The measured L*a*b* values for the 1% (circles), 5% (triangles) and 25% (squares) w/w concentration red paint samples are plotted.

L* is the lightness value component of L*a*b* according to 'CIELAB colour space' as defined by the International Commission on Illumination (CIE) where the darkest black is L*=0 and the brightest white is L*=100. The colour channels, a* and b*, represent true neutral grey values at a*=0 and b*=0. The a* value represents the green-red component, with green in the negative direction and red in the positive direction. The b* value represents the blue-yellow component, with blue in the negative direction and yellow in the positive direction.

The invention claimed is:

1. A multi-fibre optical probe for in-line spectroscopic monitoring of high concentration mediums comprising:
    at least one light detection fibre wherein each light detection fibre is configured to receive light at a light receiving end, and
    at least two illumination fibres configured to emit light from a light emitting end; wherein
    the number of illumination fibres is equal to or greater than the number of light detection fibres, and
    the light emitting ends of each of the illumination fibres are each independently positioned 50 microns or less from the light receiving end of at least one light detection fibre;
    wherein the multi-fibre optical probe does not comprise a window or other structure covering and/or in between and/or in front of any of the light emitting ends of the illumination fibres and any of the light receiving ends of the light detection fibres.

2. The multi-fibre optical probe according to claim 1 wherein the, or each, light detecting fibre and the illumination fibres independently comprise a transparent core circumferentially coated by a cladding that is 25 microns or less in thickness.

3. The multi-fibre optical probe according to claim 1 wherein the, or each, light detecting fibre and the illumination fibres are free of additives comprising germanium and/or chlorine.

4. The multi-fibre optical probe according to claim 1 wherein the number of illumination fibres is greater than the number of light detection fibres.

5. The multi-fibre optical probe according to claim 1 wherein the light receiving ends of each light detection fibre are each positioned at the same distance from the light emitting end of at least one illumination fibre.

6. The multi-fibre optical probe according to claim 1 wherein each light detection fibre is connected to a photodetector and each illumination fibre is connected to a light source.

7. The multi-fibre optical probe according to claim 6 wherein the, or each, photodetector is independently configured to detect light at wavelengths of, from UV to mid-IR.

8. The multi-fibre optical probe according to claim 6 wherein the, or each, light source is independently configured to emit light at wavelengths of, from UV to mid-IR.

9. The multi-fibre optical probe according to claim 1 wherein the total number of optical fibres is 50 or more.

10. The multi-fibre optical probe according to claim 1 wherein the ratio of light detection fibres to illumination fibres is 1 to 6 respectively.

11. The multi-fibre optical probe according to claim 1 wherein the ratio of light detection fibres to illumination fibres is 7 to 12 respectively.

12. The multi-fibre optical probe according to claim 1 wherein the light illumination fibres are arranged substantially around the one, or each, light detection fibre.

13. The multi-fibre optical probe according to claim 1 wherein each illumination fibre has a core diameter of 800 microns or less.

14. The multi-fibre optical probe according to claim 1 wherein each detection fibre has a core diameter of 800 microns or less.

15. The multi-fibre optical probe according to claim 1 wherein the optical fibres are provided substantially parallel to each another in a secured fibre bundle.

16. The multi-fibre optical probe according to claim 1 comprised in,
    an extruder wherein the optical probe is positioned at one or more of the points of solid particulate input, upstream of the point of extrusion or at the point of extrusion; or
    a milling system wherein the optical probe is positioned at one or more points of the milling surface; or
    a heterogeneous flow process at one or more of the points of input, upstream of the point of output or at the point of output.

17. A method, comprising:
    arranging in relation to a high concentration medium a multi-fibre probe for in-line spectroscopic monitoring of high concentration mediums, wherein the multi-fibre probe comprises at least one light detection fibre wherein each light detection fibre is configured to receive light at a light receiving end, and at least two illumination fibres configured to emit light from a light emitting end, wherein the number of illumination fibres is equal to or greater than the number of light detection fibres, and the light emitting ends of each of the illumination fibres are each independently positioned 50 microns or less from the light receiving end of at least one light detection fibre; and
    obtaining a spectrum of light scattered or absorbed by the high concentration medium with the multifibre probe;
    wherein the multi-fibre optical probe does not comprise a window or other structure covering and/or in between and/or in front of any of the light emitting ends of the illumination fibres and any of the light receiving ends of the light detection fibres.

18. A method of generating a predictive model for determining the value of a parameter of a solid particulate dispersion comprising:
    (i) spectroscopically analysing a plurality of reference samples of solid particulate dispersions spanning a range of values of the parameter using a multi-fibre optical probe for in-line spectroscopic monitoring of high concentration mediums, wherein the probe comprises at least one light detection fibre wherein each light detection fibre is configured to receive light at a light receiving end, and at least two illumination fibres configured to emit light from a light emitting end, wherein the number of illumination fibres is equal to or greater than the number of light detection fibres, and the light emitting ends of each of the illumination fibres are each independently positioned 50 microns or less from the light receiving end of at least one light detection fibre, wherein the multi-fibre optical probe does not comprise a window or other structure covering and/or in between and/or in front of any of the light emitting ends of the illumination fibres and any of the light receiving ends of the light detection fibres;

(ii) measuring a spectrum of each reference sample, and (iii) processing the spectra gathered in (ii) to generate a predictive model that correlates the parameter to one or more spectroscopic properties.

19. The method according to claim 18, wherein the number of reference samples is 5 or more.

20. The method according to claim 18, wherein the spectra are pre-processed before step (iii) to normalise and/or smooth the spectra.

21. The method according to claim 18, wherein the spectra of the reference samples are processed to derive a feature that correlates with the parameter across at least a portion of said range of the parameter.

22. The method according to claim 21, wherein said feature comprises:

at least a first principle component derived from principle components analysis (PCA) of all or part of the spectra or a parameter derived from the spectra, optionally wherein the variance of said first principle component by the parameter is substantially linear across the range of the parameter of said plurality of dispersions; or one or more of a lightness value L*, an a* colour value or a b* colour value of CIELAB colour space derived from the spectra.

23. A method of determining the value of a parameter of a solid particulate dispersion comprising the steps of:

(i) subjecting the dispersion to spectroscopy using a multi-fibre optical probe for in-line spectroscopic monitoring of high concentration mediums, wherein the probe comprises at least one light detection fibre wherein each light detection fibre is configured to receive light at a light receiving end, and at least two illumination fibres configured to emit light from a light emitting end, wherein the number of illumination fibres is equal to or greater than the number of light detection fibres, and the light emitting ends of each of the illumination fibres are each independently positioned 50 microns or less from the light receiving end of at least one light detection fibre, wherein the multi-fibre optical probe does not comprise a window or other structure covering and/or in between and/or in front of any of the light emitting ends of the illumination fibres and any of the light receiving ends of the light detection fibres;

(ii) measuring the spectrum of the dispersion, and (iii) determining the value of the parameter by comparing the observed spectrum to a predictive model.

24. A method according to claim 23, wherein the predictive model is for determining the value of a parameter of a solid particulate dispersion and is generated by:

(i) spectroscopically analysing a plurality of reference samples of solid particulate dispersions spanning a range of values of the parameter using the multi-fibre optical probe;

(ii) measuring a spectrum of each reference sample, and (iii) processing the spectra gathered in (ii) to generate the predictive model that correlates the parameter to one or more spectroscopic properties.

25. The method according to claim 23, wherein comparing the observed spectrum to the predictive model comprises processing the observed spectrum in the same way as the spectra of a plurality of reference samples of solid particulate dispersions spanning a range of values of the parameter, wherein processing the plurality of reference samples comprises:

(i) spectroscopically analysing the plurality of reference samples using the multi-fibre optical probe;

(ii) measuring a spectrum of each reference sample, and (iii) processing the spectra gathered in (ii) to generate the predictive model that correlates the parameter to one or more spectroscopic properties.

26. The method of claim 23, further comprising manufacturing a solid particulate dispersion by:

forming a solid particulate into a dispersion, and where the dispersion has a parameter value within an acceptable range according to the determining of the value of the parameter of the dispersion, processing the dispersion into a finished product.

27. The method according to claim 26 wherein:

the forming of the solid particulate into a dispersion is performed by extrusion; and/or the testing of the parameter value one or more times is performed in-line.

28. The method according to claim 27 wherein the forming is performed by extrusion and the testing is performed at one or more of the point of solid particulate input, upstream of the point of extrusion and at the point of extrusion.

29. The method of according to claim 18 wherein the parameter is particle loading amount, particle size distribution, particle distribution, concentration, crystallinity, colour strength and aggregation state.

30. The method according to claim 18 wherein the, or each, spectrum is measured by transmission spectroscopy.

31. The multi-fibre optical probe according to claim 3, wherein the at least one light detecting fibre and illumination fibres are each free of any additives.

32. The multi-fibre optical probe according to claim 13, wherein each illumination fibre has a core diameter of 50 microns or more.

33. The multi-fibre optical probe according to claim 14, wherein each detection fibre has a core diameter of 50 microns or more.

34. The method of claim 17, wherein the high concentration medium comprises a solid particulate dispersion, and further comprising:

determining the value of a parameter of the solid particulate dispersion by comparing the obtained spectrum to a predictive model;

wherein the parameter is particle loading amount, particle size distribution, particle distribution, concentration, crystallinity, colour strength and aggregation state.

35. The method of claim 17, wherein the spectrum is measured by transmission spectroscopy.

* * * * *